United States Patent [19]

Cannon et al.

[11] 4,259,966
[45] Apr. 7, 1981

[54] HEART RATE ANALYZER

[75] Inventors: Robert L. Cannon, Waltham; Andrew J. Griffin, Framingham, both of Mass.

[73] Assignee: American Optical Corporation, Southbridge, Mass.

[21] Appl. No.: 68,845

[22] Filed: Aug. 22, 1979

[51] Int. Cl.³ ............................................. A61N 5/04
[52] U.S. Cl. .................................................. 128/706
[58] Field of Search ............... 128/702, 703, 706, 708, 128/710, 711

[56] References Cited

U.S. PATENT DOCUMENTS

| 3,267,933 | 8/1966 | Mills et al. | 128/711 |
|---|---|---|---|
| 3,398,736 | 8/1968 | Brant et al. | 128/706 |
| 3,820,025 | 6/1974 | Lahr et al. | 128/708 |
| 4,006,737 | 2/1977 | Cherry | 128/710 |
| 4,018,219 | 4/1977 | Hojaiban | 128/706 |
| 4,022,192 | 5/1977 | Laukien | 128/706 |
| 4,034,745 | 7/1977 | Bloom | 128/706 |

Primary Examiner—William E. Kamm

Attorney, Agent, or Firm—Jeremiah J. Duggan; Alan H. Spencer

[57] ABSTRACT

A heart rate analyzer responsive to the R wave of successive ECG complexes of a patient. The intervals between successive ECG complexes are continuously counted and summed for a first number of successive complexes. First electrical representations of the average values of the intervals are generated over the first number of complexes, the number being no greater than two. The second average of the same intervals is generated for a second number of successive numbers of complexes greater than the first and electrical representations thereof are produced. These electrical representations are trapped and at least a maximum value of the first representation and a minimum value of the second representation are held. These maximum and minimum values are then converted to corresponding minimum and maximum heart rates respectively. Lastly each R wave signal generated over a predetermined period of time is counted thereby providing an indication of the average heart rate.

4 Claims, 4 Drawing Figures

HEART RATE ANALYZER

BACKGROUND OF THE INVENTION

The invention relates generally to heart rate analyzers and more particularly to a heart rate analyzer for monitoring the rate of heartbeating and for providing a visual indication of at least either the maximum or the minimum heart rate within a predetermined unit of time.

A variety of heart rate or heartbeat rate monitors and/or analyzers are known in the prior art. One type of heart rate monitor, typified by U.S. Pats. Nos. 3,948,250 and 4,083,366, compares a measured heart rate with predetermined high and low heart rate limits for the purpose of sounding an alarm if such limits are exceeded. Moreover, the average heart rate may be continually or periodically displayed.

U.S. Pat. No. 3,893,453 discloses still another type of heart rate monitor in which an average heart rate is periodically printed or scribed on a calibrated scale, as for instance ECG chart or graph paper, to show trends or changes in the heartbeat rate over a relatively long period of time. Such formating of the heat rate indications is normally termed trending for its ability to reveal, at a glance, a history of heartbeat rate changes over some relatively long period of time.

More recently, the devloping techniques of ambulatory cardiography, or Holter Cardiography as it is more commonly known, have given rise to relatively sophisticated scanners and analyzers which are utilized for scanning and analyzing tapes having ECG signals recorded therein in real time and played back at a greatly accelerated rate, i.e., 120 times speed at which recorded. These systems, typified by the American Optical Scanner Models 6002 and 6004 for Holter Cardiography, particularly Option Two thereto, marketed by American Optical Corporation, provided a sequential heart rate trend display in which the average heart rate was graphically recorded on a strip chart at one-minute intervals. A continuous record of the average heart rate is disclosed in the Holter-type scanner of U.S. Pat. No. 4,073,011. Still another Holter-type scanner of prior art has provided a bar-graph or histogram type of R-R interval display in which vertical bars indicative of some quantity of heartbeats at a particular average interval are arrayed side-by-side as a function of heart rate. Such trending of the heart rate may also be used by an analyst to facilitate retrieval, as from storage or record (as a strip chart), the particular ECG waveform(s) giving rise to the trend data.

While each of the aforementioned systems does provide some degree of insight into a patient's heart rate, the particular heart rate information displayed usually tends to be rather coarse and does not afford a closer analysis of heart rate excursions over relaively short intervals of time.

In addition to some of the more conventional information which may be gleaned by a physician through analysis of a histogram or other type of trend display showing a patient's heart rate, certain further information of particular significance might be obtained if the physician or operator is able to rapidly and accurately determine the occurrence of so-called "dropped beats". It is felt by some that a close relation exists between the occurrence of dropped or omitted heartbeats and the existence of second degree heart block. This latter condition is one which is relatively readily treatable by the installation of a pacemaker, and thus the detection of second degree AV heart block is particularly significant. The conventional Holter monitoring technique, in which an operator watches a rapidly displayed sequence of superimposed ECG complexes, has not lent itself to the easy detection of dropped beats by the operator, and the graphical recording of every ECG complex for later review consumes considerable time and paper, as well as still requiring a slow review by an analyst.

Accordingly, it is a principal object of the present invention to provide a heart rate analyzer which is capable of providing a visual indication of at least either the maximum or the minimum heart rate of a patient within a predetermined unit of time. Moreover, it is a further object to provide visual indications of both the maximum and the minimum heart rate within the predetermined unit of time.

A further object of the invention is the provision of visual indications of the maximum and minimum heart rates occurring within predetermined units of time of such duration that valuable information is readily retrievable.

It is a still further object of the present invention to determine the maximum and the minimum heart rates determined within a predetermined unit of time in a manner facilitating the identification and/or retrieval of "dropped beats" from the stored or recorded ECG waveforms.

SUMMARY OF THE INVENTION

The foregoing and other objects of the invention are accomplished by providing a heart rate analyzer which detects the R-waves in successive ECG complexes and generates signals coincident with the detection of the R-waves and to then use such R-wave indicating signals for generating electrical representations of at least one, or preferably both, of the maximum and the minimum heart rates within a predetermined unit of time. The maximum and/or minimum heart rate representations are then utilized to provide a visual indication of the maximum and/or minimum heart rates of the patient.

More specifically, the heart rate analyzer of a preferred embodiment of the invention is capable of determining the maximum, minimum and average heart rates of a patient, as for instance from Holter-type recordings, over predetermined units of time or intervals, as for instance each minute, and then graphically recording those determined values on a strip chart to afford relatively fast, simple and accurate interpretation by the operator or physician scanning the charts and to facilitate retrieval of the actual ECG waveforms which resulted in the displayed rates.

In providing for the determination and display of maximum and minimumm heart rates, an average heart rate over a relatively brief interval, i.e., several seconds, may be provided and continuously updated, which average rate is then tracked over the predetermined unit of time in a manner which notes and holds the highest and lowest heart rates respectively within that unit of time. These values are then available as the indications of maximum and minimum heart rate for that predetermined unit of time, i.e., one minute.

In another embodiment of the invention, the average interval between a predetermined plurality of successive R-waves is tracked over the predetermined unit of time and the maximum and/or minimum interval is held and subsequently converted to an indication of minimum and/or maximum heart rate respectively. More specifically, the interval between successive R-waves is preferably formulated as an average, which average is determined in the instance of minimum heart rate by averaging the intervals between a small number, i.e., one or two, of successive R-waves and which average is determined in the instance of maximum heart rate by averaging the intervals between a significantly larger number, i.e., eight, of successive R-waves. By using a two or two-beat interval for the average used in determining the minimum heart rate, a dropped beat will have a significant impact on the minimum heart rate value which is displayed, thus facilitating its identification and retrieval. Further, the larger number of beats over which the interbeat interval is averaged for determining maximum heart rate serves to diminish the effect of artifact, which is usually of high rate.

DESCRIPTION OF THE PREFERRED EMBODIMENTS

Figure 1:
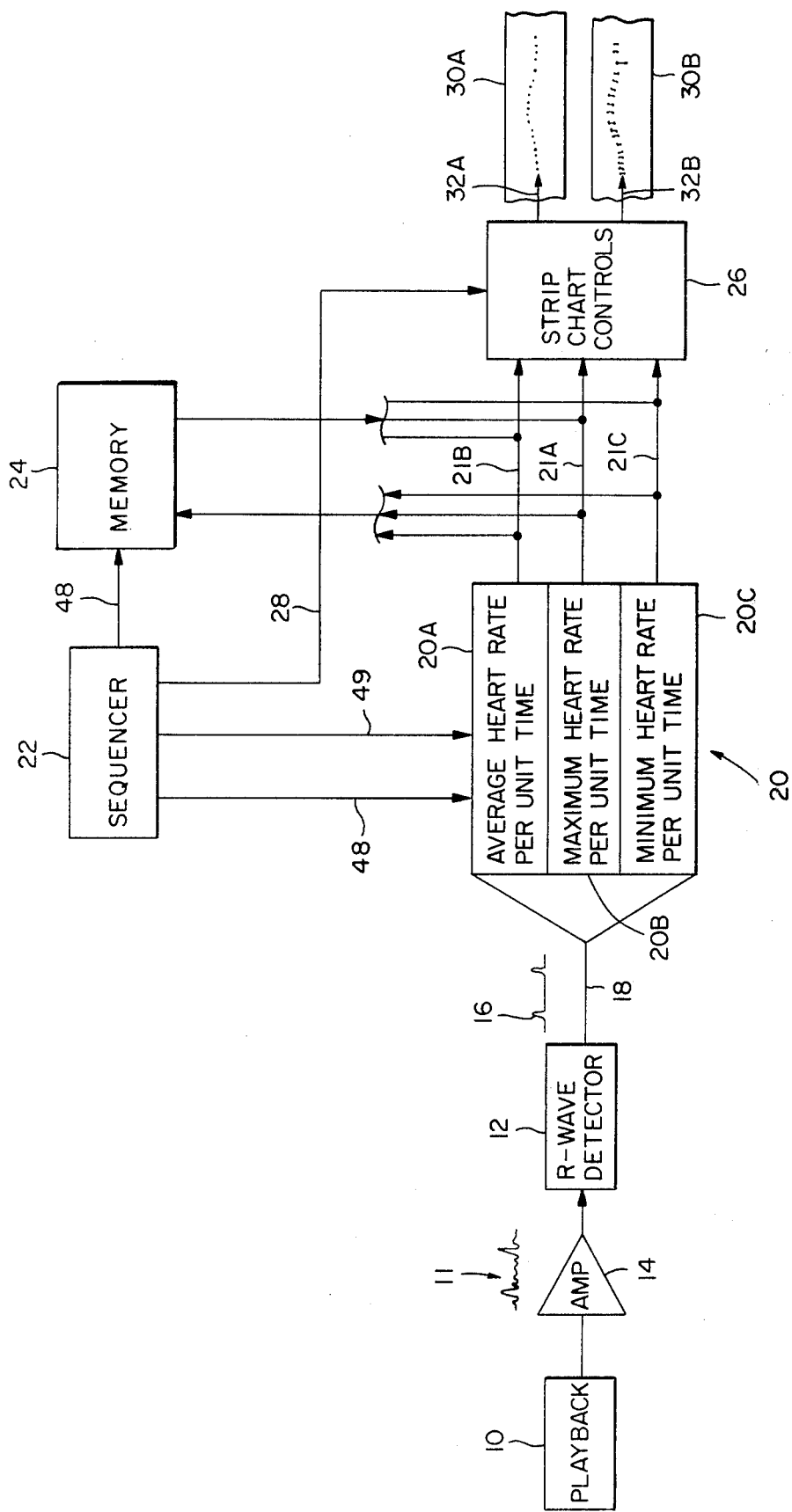
FIG. 1 is a functional block diagram showing a heart rate analyzer for providing particular heart rate displays in accordance with the invention.

Referring now to FIG. 1, there is illustrated a heart rate analyzer in accordance with the invention and particularly suited for use in scanning or analyzing ECG signals recorded on a magnetic tape in accordance with the known principles of ambulatory or Holter-type electrocardiography. Further still, the novel heart rate analyzer includes provision for displaying, as by graphical recording and the like, the maximum and minimum heart rate per unit of time, i.e., per minute, in addition to the more traditional display of average heart rate. Such display of maximum, minimum and average heart rate following predetermined units or intervals of time results in a trending of the maximum, minimum and average heart rates, thereby affording the analyst with a relatively detailed but easily used and understood record of a patient's heart rate. This record facilitates retrieval of the relevant ECG waveforms from storage, as on a magnetic tape or strip chart. This is particularly the case wherein the display of heart rate may be permanently recorded, as on special, concise strip charts bearing identifying time data printed thereon for correlating the trended heart rates and other relevant analytical data with the ECG waveforms giving rise thereto. The ECG waveforms are normally stored on magnetic tape, and may be graphically recorded on separate strip charts for the periods of interest.

Although not limited thereto, the heart rate analyzer of the present invention finds particular application in ambulatory cardiography in which ECG signals recorded on a magnetic tape at one speed are played back at a substantially higher speed, i.e., 60 times or preferably 120 times the recording speed, for the scanning and analysis function. Accordingly, a suitable tape playback unit 10 supplies ECG signals 11 to a suitable R-wave detector 12 of known design via suitable preamplifier-amplifier 14. The R-wave detector 12 responds to the QRS complex in each PQRST waveform in the ECG singal to indicate the occurrence of an R-wave. The output of R-wave detector 12 may typically be an electrical pulse 16 coinciding with the occurrence of an R-wave. The R-wave-indicating pulses 16 are then extended via lead 18 as an input to heart rate calculator 20. The heart rate calculator 20 in the general embodiment of FIG. 1 serves to convert the R-wave-indicating signals to representations of the maximum heart rate, the minimum heart rate and the average heart rate per some predetermined unit, or units, of time. In the present embodiment, the predetermined unit of time or interval for each of the aforementioned heart rates is chosen as one minute referenced to the patient, such interval being sufficiently short to provide a sufficient quantity of meaningful information and yet sufficiently long that the subsequent graphical portrayal may be relatively compact and easily read. The heart rate calculator 20 may be considered as comprising an average heart rate calculator 20A, a maximum heart rate calculator 20B and a minimum heart rate calculator 20C. The average heart rate calculator 20A determines the average heart rate at one-minute intervals for the preceding thirty seconds or more in a known manner. The maximum and minimum heart rate calculators 20B and 20C respectively, however, also provide indications of the maximum heart rate and the minimum heart rate at one-minute intervals for the preceding one minute. The sampling of heart rate outputs at one-minute intervals is done under the control of a sequencer 22 as taught by various prior art systems including the aforementioned American Optical Scanner Models 6002 and 6004, Option Two. Sequencer 22 may include clock circuitry or other suitable timing means for interrogating the heart rate calculator 20 at one-minute intervals. More specifically, the sequencer 22 may act in synchronization with a timing code appearing on a separate channel (not shown) of the recorded signal which is played back by unit 10. The timing code provides means for correlating the occurrence of specific ECG signals with the resulting heart rate outputs from calculator 20. In the formatting of the display of certain types of heart trend data, it is known to print an hourly indication of time along the margin of the strip chart in registry with certain data being trended on the chart. Further, cumulative data for each hour may be edge-printed between each two relevant hour time markers. However, to do this, it is necessary to delay the output for an hour, referenced to the patient. This delay is also applied to the heart rate trend data which is to be displayed in registry with the appropriate time markers. Therefor, a memory 24 may be employed to temporarily store and thereby delay the transmission of the heart rate data from calculator 20 to a graphical display system such as strip chart recorder controls 26.

The strip chart controls 26 illustrated in FIG. 1 are substantially of a known type,, for instance substantially as illustrated and described in U.S. Pat. No. 3,894,533 to Robert L. Cannon and assigned to American Optical Corporation, which patent is incorporated herein by reference. Generally speaking, the heart rate data either directly from calculator 20 or via the delay means of memory 24 is provided to appropriate inputs of the strip chart controls 26, as is a timing input from sequences 22 via lead 28 such that the electrical heart rate representations are translated into indicia graphically recorded on strip charts 30A and 30B through the use of some writing means such as ink or thermal styli 32A, 32B respectively. In the embodiment illustrated herein and described in greater detail under the reference to FIG. 3, the average heart rate is written on one strip chart 30A or one channel of multi-channel chart paper and the maximum and minimum heart rates are written on another strip chart 30B or another channel of multi-channel chart paper. While this is done in the present instance to permit the portrayal of other information (not shown) on each of the two chart paper display channels, it will be appreciated that in certain instances the two channels may be merged into one.

Figure 2:
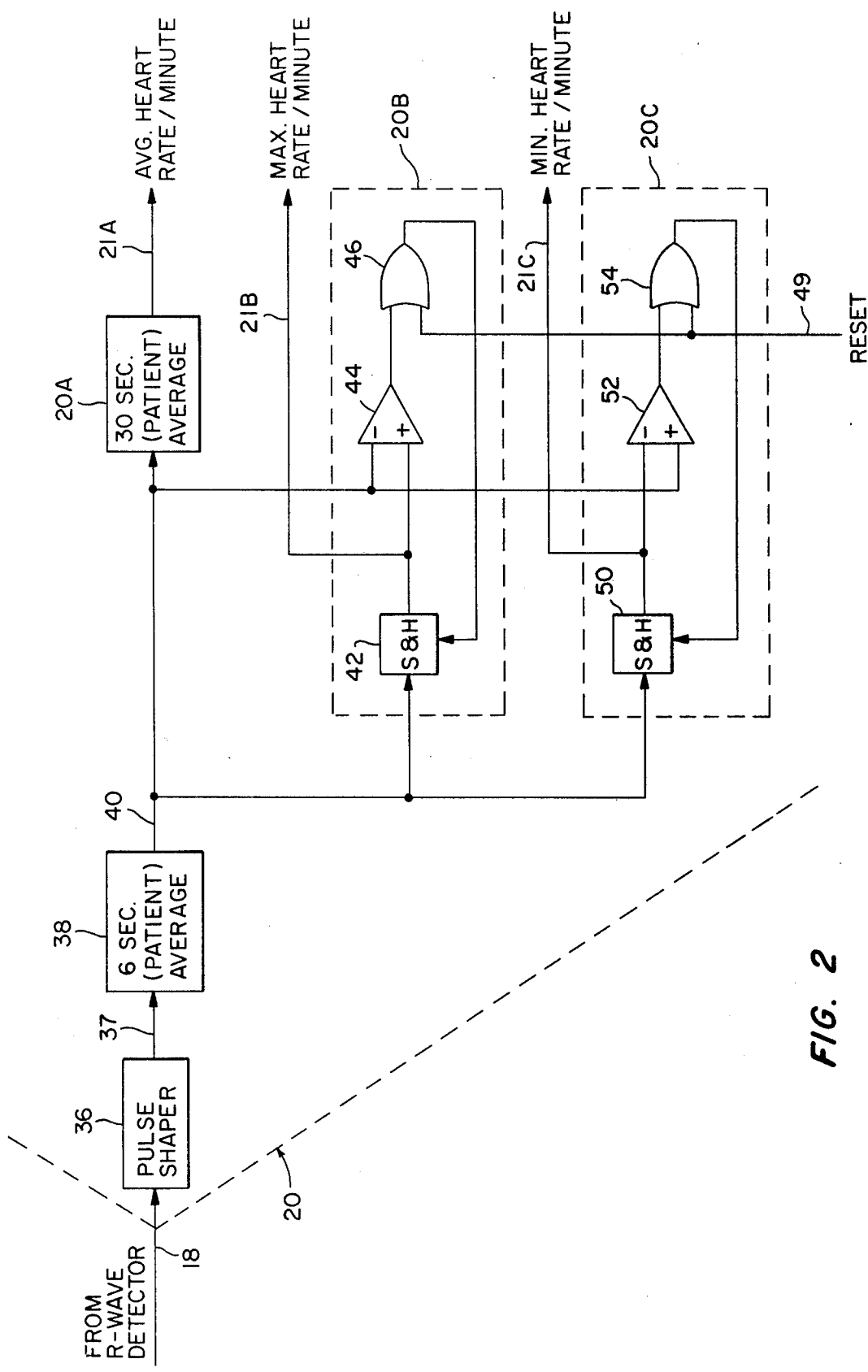
FIG. 2 is a more detailed functional block diagram and circuit schematic of a novel portion of the system of FIG. 1 in accordance with one embodiment of the invention.

Referring to FIG. 2, one embodiment of the heart rate calculator 20 of FIG. 1 is illustrated in greater detail. The R-wave-indicating pulses appearing on lead 18 are extended to suitable pulse-shaping circuitry 36 for providing pulses of standardized amplitude and duration in a known manner in response to respective R-wave indications. These now-standardized R-wave-indicating pulses are inputted via lead 37 to a six-second averaging circuit 38 which may conveniently comprise a low pass filter having the appropriate time constant. The six-second average referred to in averaging circuit 38 will, for purposes of describing the invention, refer to six seconds of real, or patient, time; however, it will be appreciated that the constants selected for the filter would in fact develop a one-tenth of a second average if the playback speed were 60 times the recording speed and would be one-twentieth of a second average if the playback speed were 120 times the recording speed. Similarly, other averaging intervals referred to hereinafter will be referenced to real, or patient, time but will be scaled accordingly for speeded-up playback time. The output 40 of six-second averaging circuit 38 represents the average heart rate over the immediately past six-second interval. This value is extended to the inputs of the average heart rate calculator 20A, the maximum heart rate calculator 20B and the minimum heart rate calculator 20C. The six-second average of averager 38 is selected to be sufficiently short that the low rate variations appear yet sufficiently long that the effects of high rate or high frequency aberrations are minimized.

In providing the average heart rate output from calculator 20A, the six-second average from averager 38 is in turn applied to a 30-second averaging circuit 20A. Circuit 20A provides an average over a substantial portion of the one-minute reporting interval, and might be chosen to be as short as 20 seconds, or as long as 60 seconds or more, 30 seconds having been chosen herein for design convenience. The 30-second averaging circuit 20A provides its output on lead 21A which in turn is sampled under the control of sequencer 22 for temporary storage in memory 24 or direct application to the strip chart controls circuitry 26. In the event the output of average heart rate circuit 20A is to be stored in memory, it will be converted from analog to digital form, then stored in memory, then converted from digital to analog form for application to strip chart controls circuitry 26.

The FIG. 2 circuitry of maximum heart rate and minimum heart rate calculators 20B and 20C respectively are quite similar to one another, both comprising track-and-hold circuits and differing from one another only in the complementary nature of their respective comparators for determining maximum and minimum. The maximum heart rate calculator 20B includes a sample-and-hold circuit 42 receiving the output 40 from six-second averager 38. The output of sample-and-hold circuit 42 is extended to the positive or non-inverting input of a comparator 44 having its output connected as an input of OR gate 46. The output of OR gate 46 is fed back to sample-and-hold circuit 42. The other, or negative, input to comparator 44 is provided by the output 40 of averager 38. In this manner the immediate average appearing on lead 40 appears on the negative input of comparator 44 and the stored or held value of sample-and-hold circuit 42 appears on the positive input of the comparator. Whenever the present six-second average is less than the value stored in sample-and-hold circuit 42, the output of the comparator 44 is a logic zero and no control signal is fed back through OR gate 46 to sample-and-hold circuit 42. On the other hand, however, when the present output of six-second averager 38 is greater than the highest average stored in sample-and-hold circuit 42, the output comparator 44 goes to a logic one which in turn is passed through OR gate 46 to the control input of sample-and-hold circuit 42. This fed-back control signal serves to enter this new maximum heart rate value in the sample-and-hold circuit 42 and thereby replace the older lower value formerly stored therein. Thus, whenever a higher six-second heart rate average appears, it will be stored in sample-and-hold circuit 42 and similarly appears on the output 21B thereof designated maximum heart rate.

Assuming the predetermined interval or unit of time between successive writeout or printng of maximum heart rate is one minute, the sequencer 22 of FIG. 1 will provide strobe and reset control signals generally represented as appearing on conductors 48 and 49 respectively, at one-minute intervals. Typically the strobe signal is operative to first temporarily store the maximum heart rate signal appearing on lead 21B either by means of memory 24 or temporary storage circuitry associated with strip chart controls 26. Immediately thereafter the reset signal appearing on lead 48 is extended through another input to OR gate 46 to the control input of sample-and-hold circuit 42 such that whatever six-second average value is appearing at the input to the sample-and-hold circuit is stored therein at that moment. This newly stored value in sample-and-hold circuit 42 represents the first heart rate of the next minute and will be retained throughout that minute only if a more rapid six-second average heart rate does not occur to replace it during the minute.

Similarly, the output 40 of six-second averager 38 is extended to the input of sample-and-hold circuit 50 of minimum heart rate calculator 20C. The output of sample-and-hold circuit 50 is extended to the negative or inverting input of a comparator 52 having its output extended as an input to OR gate 54. The output of OR gate 54 is fed back as the control input to sample-and-hold circuit 50. The present six-second average signal appearing on lead 40 is extended to the positive or non-inverting input of comparator 52 such that comparator 52 provides a logic one output only when the present six-second heart rate average is less than the value stored in sample-and-hold circuit 50. In such instance, that present six-second average also appearing at the input to sample-and-hold circuit 50 is loaded thereinto by the control signal. Accordingly, the output 21C of sample-and-hold circuit 50 represents the minimum heart rate. As with the maximum heart rate and the average heart rate, the strobe pulse on lead 48 from sequencer 22 serves to temporarily store, either in memory 24 or strip chart control circuitry 26, the minimum heart rate determined for the preceding minute. Thus there are provided to the strip chart control circuitry 26 electrical signals, normally in analog form, representative of the average heart rate, the maximum heart rate and the minimum heart rate for the preceding minute (real, or patient, time) of heart activity. The timing pulse on lead 28 recurs at one-minute intervals in synchronization with strobe pulse on lead 48 to provide master timing for strip chart control circuitry 26.

Figure 3:
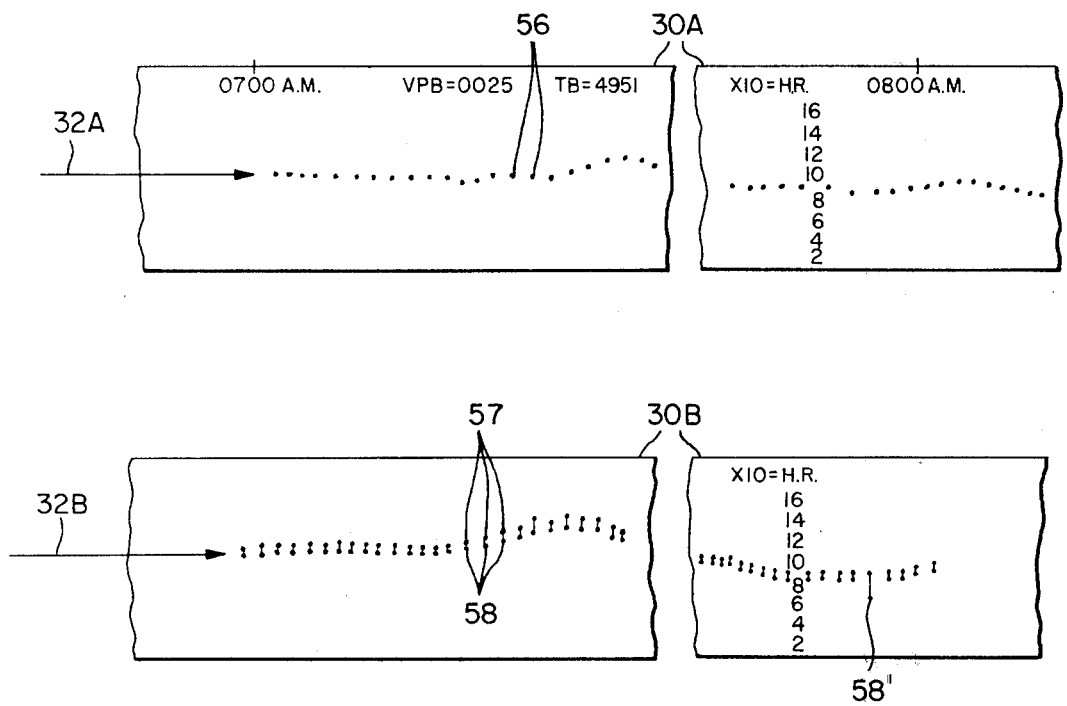
FIG. 3 is an illustrative embodiment of the graphical record of the present invention, the record depicting maximum and minimum heart rate per unit of time as well as average heart rate.

Referring to FIG. 3, the average heart rate per minute signal 21A may be connected such that it controls the stylus 32A for writing average heart rate indicia 56 on strip chart channel 30A. Further, the maximum and minimum heart rate signals on 21B and 21C respectively are connected to the strip chart control circuitry 26 such that through stylus 32B they control the writing of maximum and minimum heart rate indicia 57 and 58 respectively on strip chart 30B. As disclosed in the aforementioned U.S. Pat. No. 3,894,533, the deflection of a stylus 32A or 32B is controlled by a respective galvanometer receiving the appropriate heart rate control signal at its input. A mark may be made on the strip chart by the application of a small amplitude dithering signal in a known manner to the galvanometer control circuitry. Moreover, where dual values such as maximum heart rate and minimum heart rate appear in the same time frame on strip chart 30B, the maximum value might be first written, then the stylus 32B would be slowly slewed toward zero but would be stopped at the position representative of the minimum heart rate whereupon a dithering signal applied to the galvanometer would write that indicia 58. During the slewing operation, the stylus 32B may be controlled to write a light connection line between the maximum and minimum heart rate indicia. In contrast with the stepped advance of the chart paper in the aforementioned Patent 3,894,533, the chart paper 30A, 30B in the present embodiment is continuously advanced by a chart advance motor (not shown) under the control of the sequencer 22. The styli 32A, 32B may be lifted from chart paper 30A, 30B during the greater portion of each minute and are placed in operative writing orientation therewith only during a short interval at the end of each minute. In this way, average, maximum and minimum heart rate indicia 56, 57 and 58 respectively are written on the strip charts 30A, 30B at horizontally spaced intervals corresponding with one-minute intervals of real patient time. Additional data such as patient time, ventricular premature beats (VPB), total heartbeats, etc., may be written in the margins of the strip charts at longer intervals, such as each hour.

Figure 4:
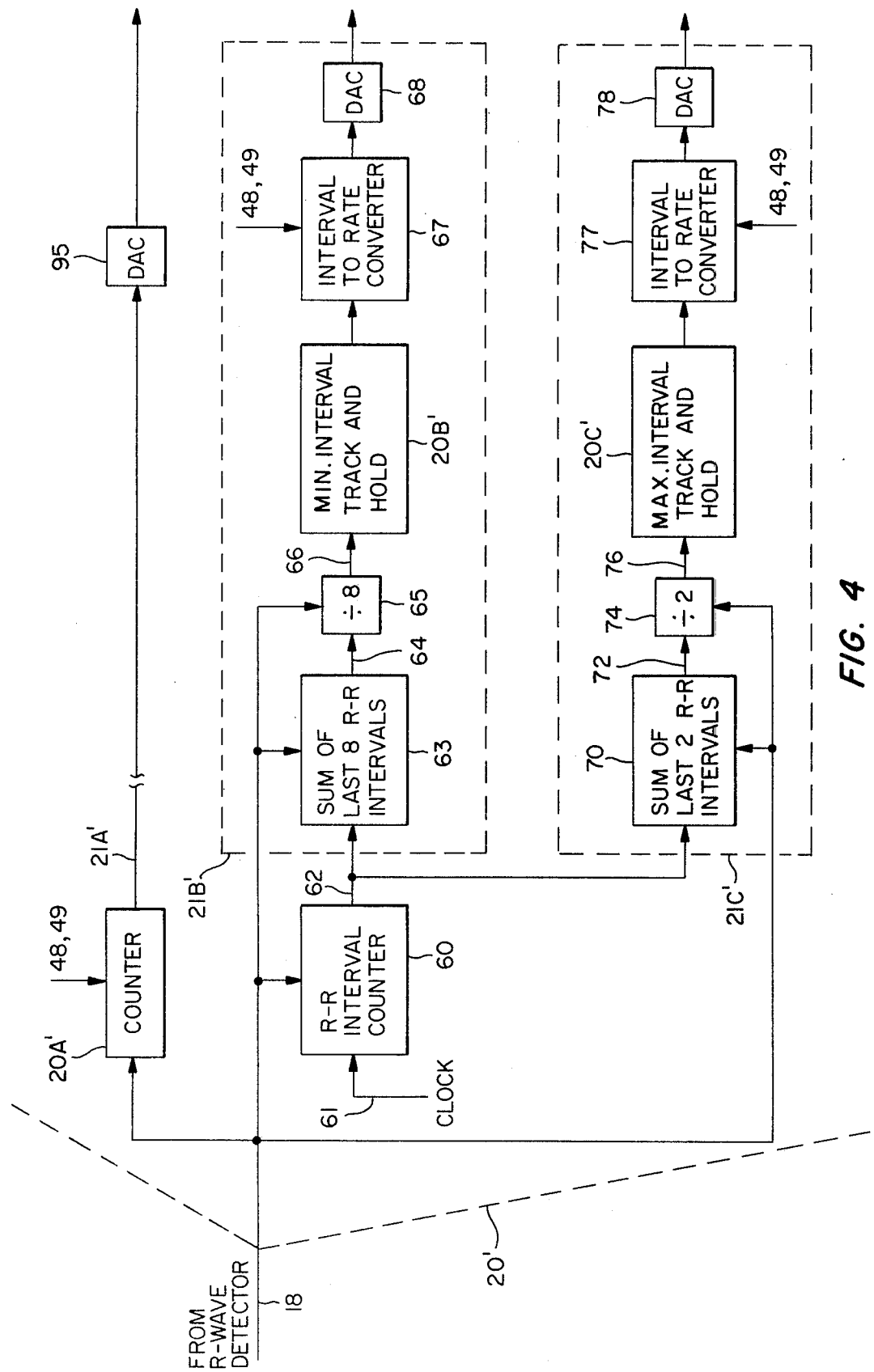
FIG. 4 is a more detailed functional block diagram and circuit schematic of a novel portion of the system of FIG. 1 in accordance with another embodiment of the invention.

Referring now to FIG. 4, there is illustrated an alternate embodiment of the heart rate calculator designated 20' therein. Instead of developing both the maximum and minimum heart rate signals using a six-second average analog signal as from circuit 38 of FIG. 2, the present embodiment determines heart rate based on the interval between successive R-waves, i.e., the R-R interval. More specifically, the maximum heart rate per minute is determined utilizing an average of the most recent eight R-R intervals and the minimum heart rate is determined using an average based on the most recent two R-R intervals. The foregoing arrangement is desirable because it minimizes the effect of artifact which tends usually to occur at a high rate and it further emphasizes the occurrence of a dropped heartbeat by its significant impact on the minimum heart rate value.

The heart rate calculator 25 of FIG. 4 is further contrasted with the calculator 20 of FIG. 2 in that it performs most of its functions in the digital rather than the analog domain. Specifically, output 18 of R-wave detector 12 is applied to the clocking input of a multi-stage counters 28' for registering the number of R-wave pulses occurring during predetermined unit of time, i.e., one minute. It will be appreciated that as the computations herein are performed in the digital domain through the use of counters, there is no need to standardize the amplitude and width of the R-wave pulses and thus pulse shaper 36 of FIG. 2 may be omitted, the non-standardized waveshapes 16 of the R-wave detector 12 being sufficient to control the respective counters. Counter 28' receives strobe and reset control signals 48, 49 serving substantially the same function as described above. Thus, at the end of each minute, counter 28' will receive a strobe pulse 48 for either transferring the count to a memory 24 or passing it directly to strip chart control circuitry 26 via a digital-to-analog converter 95. The strobe pulse 48 is immediately followed by a reset pulse 49 for zeroing the counter 28'. Thus each minute there is provided on lead 21A' an electrical representation of the number of heartbeats and thus heart rate for the preceding minute. This actual count over a one-minute interval is thus utilized as the average rate for that minute.

The R-wave pulses 18 are similarly applied to a reset input of an R-R interval counter 60 which also receives a predetermined clock signal 61 at its clocking input. The clock signal 61 is provided by a clock source associated with sequencer 22 and is of sufficiently high frequency that the output count of R-R interval counter 60 is capable of reflecting relatively small changes in the R-R interval. The output 62 of R-R interval counter 60 is applied to summing circuitry 63 of suitable design which provides an output 64 indicative of the sum of the last (most recent) eight R-R intervals. Typically the summing circuitry 63 will comprise a series of eight registers, each of which contains a different one of the last eight R-R intervals, and appropriate adders for summing those eight intervals. As each new R-R interval is determined, that value replaces the oldest R-R interval stored in one of the eight registers. The sum 64 of the last eight R-R intervals is extended to divide-by-eight circuitry 65 of suitable known design such that the output 66 therefrom represents the average of an R-R interval based on the eight immediately past R-R intervals. That average R-R interval is extended via lead 66 to the input of a minimum interval track-and-hold circuit 20B' which is generally similar to the track-and-hold circuit 20B of the FIG. 2 embodiment. The R-wave pulses 18 are also extended to the strobe and/or reset inputs of the summer 63 and divider 65 to effect the requisite shifting of data and/or resetting of counters.

More specifically, the track-and-hold circuit 20B' serves to track and hold the minimum interval occurring during successive one-minute sampling intervals. The minimum interval finally appearing at the output of track-and-hold circuit 20B' at the end of each minute is converted to its corresponding heart rate value, which value corresponds with the maximum heart rate occurring during the preceding minute. The conversion from minimum R-R interval to maximum heart rate is effected by suitable conversion circuitry 67 of known design which is controlled by appropriate strobe and reset control signals 48, 49 as described above. Thus the output of conversion circuit 67 corresponds with the maximum heart rate per minute, which signal may then be temporarily stored in memory 24 or directly extended to digital-to-analog conversion circuit 68 for conversion to an analog signal value which is then applied to strip chart control circuit 26 as described above.

The output 62 of R-R interval counter 60 is also extended to a minimum heart rate calculator circuit 21C′, and specifically to the input of summing circuit 70 for summing the last two R-R intervals. Circuit 70 is similar to circuit 63 but is only required to sum the immediately past two R-R intervals, which sum is then extended via lead 72 to a divide-by-two circuit 74 which provides at its output 76 an R-R interval value based on the average of the last two R-R interval values. As for the maximum heart rate calculator, the R-wave pulses are extended to summer 70 and divider 74 to effect the requisite shifting of data and/or resetting of counters.

The three-beat average R-R interval value 76 is extended to the input of a maximum interval track-and-hold circuit 20C′ which generally corresponds with the track-and-hold circuit 21C of FIG. 2. The value of the signal appearing at the output of track-and-hold circuit 20C′ at the end of each minute interval corresponds with the maximum average R-R interval occurring during that minute and is in turn converted by converting circuit 77 to the corresponding heart rate, which heart rate represents a minimum heart rate occurring during the minute interval. The strobe and reset pulses 48, 49 are similarly applied to conversion circuit 77. As with the maximum heart rate signal, the minimum heart rate signal of calculator circuit 21C′ may be extended for temporary storage to memory 24′ or may be directly converted from its digital value to its analog value by digital-to-analog converter 78 whereupon it is applied to the appropriate input to strip chart control circuitry 26.

It will be appreciated that by basing the minimum heart rate on the average interval of only one, or in the present instance two, R-R intervals, the effects of a dropped beat are quite pronounced on the average interval value and accordingly on the corresponding minimum heart rate value. In the present instance, assuming a heart rate of 60 beats per minute and therefore an actual and an average R-R interval of one second, a single dropped beat will extend the average R-R interval to one and one-half seconds, thereby creating an apparent 33% reduction in the minimum heart rate value, or in other words, 40 beats per minute. Such a significant change in the R-R interval or heart rate is clearly evident in the corresponding written minimum heart rate indicium 58′, thereby calling the observer's attention to the ECG waveforms obtained during the preceding minute of time. Those waveforms may then be retrieved from storage and presented on a CRT display and/or a graphic recorder for a careful and detailed analysis to identify the situation giving rise to the apparent dropped heartbeat. Although an "average" R-R interval based on a single R-R interval (i.e., two successive beats) would provide even greater sensitivity, the present average developed from two R-R intervals is sufficiently sensitive and is preferred because it is less sensitive to artifact. For example, it is preferable that a premature ventricular beat followed by a long (i.e., compensatory) pause not be construed as involving a dropped beat.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A heart rate analyzer comprising means responsive to the R-wave of successive ECG complexes of a patient for generating signals coincident with the ocurrence of each of said R-waves, first means responsive to said R-wave signals for counting each interval between successive R-wave signals, first means responsive to said counting means for continuously summing said intervals for a first number of successive R-wave signals and for generating first electrical representations of the average of said intervals over said first number of successive R-waves, said first number of successive R-waves being no greater than two, second means responsive to said counting means for continuously summing said intervals for a second number of R-waves greater than said first number and for generating second electrical representations of the average of said intervals over said second number of successive R-waves, means for tracking said first and second representations and for holding at least a maximum value of said first representation and a minimum value of said second representation, means responsive to said maximum and minimum values for converting said values to minimum and maximum heart rates respectively, and second means for counting each said R-wave signal generated over a predetermined unit of time.

2. The analyzer of claim 1 wherein said second plurality of successive R-waves is eight.

3. The heart rate analyzer of claim 2 including means responsive to said second counting means for continuously generating third electrical representations of the number of said R-wave signals generated over said predetermined unit of time, thereby producing an average heart rate signal over said predetermined period of time.

4. The heart rate analyzer of claim 3 including digital-to-analog converter means for generating electrical analogs of said first, second and third representations respectively.

* * * * *